(12) United States Patent
Flasinski

(10) Patent No.: US 7,528,246 B2
(45) Date of Patent: May 5, 2009

(54) ACTIN REGULATORY ELEMENTS FOR USE IN PLANTS

(75) Inventor: Stanislaw Flasinski, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 11/801,133

(22) Filed: May 8, 2007

(65) Prior Publication Data

US 2008/0039324 A1    Feb. 14, 2008

Related U.S. Application Data

(62) Division of application No. 10/950,233, filed on Sep. 24, 2004, now Pat. No. 7,408,054.

(60) Provisional application No. 60/505,949, filed on Sep. 25, 2003.

(51) Int. Cl.
    *C12N 15/82* (2006.01)
    *C12N 15/63* (2006.01)
    *C12N 15/09* (2006.01)
    *A01H 5/10* (2006.01)

(52) U.S. Cl. .............. 536/24.1; 536/23.1; 800/278; 800/298; 800/320; 435/320.1

(58) Field of Classification Search .............. None
    See application file for complete search history.

(56) References Cited

U.S. PATENT DOCUMENTS

| | | | | |
|---|---|---|---|---|
| 5,094,945 | A | * | 3/1992 | Comai .......................... 435/6 |
| 5,312,910 | A | | 5/1994 | Kishore et al. .............. 536/23.2 |
| 5,463,175 | A | | 10/1995 | Barry et al. .................. 800/300 |
| 5,489,520 | A | | 2/1996 | Adams et al. ................ 800/293 |
| 5,627,061 | A | | 5/1997 | Barry et al. .................. 800/288 |
| 5,633,435 | A | | 5/1997 | Barry et al. .................. 800/288 |
| 5,641,876 | A | * | 6/1997 | McElroy et al. ............. 536/24.1 |
| 6,040,497 | A | | 3/2000 | Spencer et al. .............. 800/288 |
| 2003/0083480 | A1 | | 5/2003 | Castle et al. ................ 536/23.1 |
| 2006/0162010 | A1 | | 7/2006 | Flasinski .................... 800/278 |

FOREIGN PATENT DOCUMENTS

| WO | WO 91/09948 | 7/1991 |
| WO | WO 98/44140 | 10/1998 |
| WO | WO 00/20571 | 4/2000 |
| WO | WO 00/70067 | 11/2000 |

OTHER PUBLICATIONS

Kim et al 1994, Plant Molecular Biology 24:105-117, provided on Applicant IDS.*
Donald et al 1990, EMBO J. 9:1717-1726, provided on Applicant IDS.*
Dolferus et al 1994, Plant Physiology 105:1075-1087, provided on Applicant IDS.*
McElroy et al. Plant Cell 1990 vol. 2 pp. 163-171.*
Wang et al 1992 Molecular and Cellular Biology 12:339-3406.*
An et al., "Strong, constitutive expression of the Arabidopsis ACT2/ACT8 actin subclass in vegetative tissues," *The Plant Journal*, 10:107-121, 1996.
Database EMBL Accession No. AP003263, Feb. 22, 2001.
Dolferus et al., "Differential interactions of promoter elements in stress responses of the arabidopsis Adh gene," *Plant Physiology*, 105:1075-1087, 1994.
Donald et al., "Mutation of either G box or I box sequences profoundly affects expression from the arabidopsis rbcS-1A promoter," *EMBO J.*, 9:1717-1726, 1990.
GenBank accession No. X15862.
GenBank accession No. X15863
GenBank accession No. X15864.
GenBank accession No. X15865.
Kim et al., "A 20 nucleotide upstream element is essential for the nopaline synthase (nos) promoter activity," *Plant Molecular Biology*, 24:105-117, 1994.
McElroy et al., "Characterization of the rice (*Oryza sativa*) actin gene family," *Plant Mol. Biol.*, 15:257-268, 1990.
McElroy et al., "Construction of expression vectors based on the rice actin 1 (Act1) 5' region for use in monocot transformation," *Mol. Gen. Genet.*, 231:150-160, 1991.
McElroy et al., "Isolation of an efficient actin promoter for use in rice transformation," *Plant Cell*, 2:163-171, 1990.
McElroy et al., "Structural characterization of a rice actin gene," *Plant Mol. Biol.*, 14:163-171, 1990.
Meagher, "Divergence and differential expression of actin gene families in higher plants," *Int. Rev. Cytol.*, 125:139-163, 1991.
Moniz de sa et al., "Phylogeny and substitution rates of angiosperm actin genes," *Molecular Biology and Evolution*, 13(9):1198-1212, 1996.
Reece et al., "Genomic nucleotide sequence of four rice (*Oryza sativa*) actin genes," *Plant Mol. Biol.*, 14:621-624, 1990.
Reece, "The actin gene family of rice (*Oryza sativa L*)," Ph.D. thesis, Cornell University, Ithaca, NY, 1988.
Zhang et al., "Analysis of rice Act1 5' region activity in transgenic rice plants," *Plant Cell*, 3:1155-1165, 1991.

* cited by examiner

*Primary Examiner*—Russell Kallis
*Assistant Examiner*—Brent Page
(74) *Attorney, Agent, or Firm*—Pamela J. Sisson; Sonnenschein Nath & Rosenthal LLP

(57) ABSTRACT

The present invention provides polynucleotide molecules isolated from *Oryza sativa* and *Zea mays* and useful for expressing transgenes in plants. The present invention also provides expression constructs containing the polynucleotide molecules useful for expressing transgenes in plants. The present invention also provides transgenic plants and seeds containing the polynucleotide molecules useful for expressing transgenes in plants.

16 Claims, 7 Drawing Sheets

SEQUENCE LISTING

```
<160> NUMBER OF SEQ ID NOS: 7

<210> SEQ ID NO 1
<211> LENGTH: 1874
<212> TYPE: DNA
<213> ORGANISM: Oryza sativa

<400> SEQUENCE: 1
ggccgcccac tattccggat cgaattgcca cgtaagcgct acgtcaatgc cacgccagat      60
gaagacctga gtcaaattag ccacataggc gccacgtcag ccaaaaccac ccttaaaacc     120
acaaggacct aatctgcacc ggtttttaata gttgagggac ccagtgtgtc tggttttctg    180
gttgagggac gaaaatcgga ttcggattcg ttgacaagtt aagagacctc atatgaactt    240
atttcttcct tgtttggttc gacctcgatc ggggttgagt gggctgtggc ggtgaaatcg    300
agcccaaatc gacagttgca gcatggtcca aagcgagccc aaaatcaaca agaaggccgg    360
```

```
cccaaaggct gaggcccatg gacagctgca gccatcaaag ccgccccacc aacacaactc    420
cccacgaggc cccgagcata tcatcgcctt cgccgcaaag tcccaacact agcggcgacc    480
ggcgaggact ccgycggcga cgtgggtggg actgagaagc gccgccgctg acaccagcga    540
gacgaggcgg cgacctccgt tgacggtaac ctacctacca acctcgccat tcctctccaa    600
actgttgtgc tgctgtctag atctcccaca ctacactagt tactcctcgt agatctcggc    660
tacctggctc aagatccggg gtcagatccg gtccggggga ttttctttgt gccctatggc    720
tgtattttgg cgtctgtggc tgatgacagc gtgtgttctc gagtgcggat gcaatctgag    780 ttataggc aaatggcctt gtcaactcgg gcagcggcat tgctttgctc agtgtgtttg    840
aatgtgctga aattcatgta gtaggctgta ggctgtgcat tcttgatttt gcgtcttgca    900
taattcactg gtggatttc taaacctaac aagtttaaaa ttagaccatt caaccaaaga    960
caggaggaat aagtgaagct gttgtagtca cagcttatgg ccgatccaaa atttgttagg   1020
aatgtgaata tgtgatgcta caaacatatc cttgtaagct accatgctat ttatcatgtt   1080
ccatcatggt gattggtgag cactcatgaa aatttcagat ccaaacctag tgttacatgt   1140
ggatttgtgc tctgcaatct atcgccagta ataaaatggt tgagtgatcc agctactaca   1200
aaatcacatt gcatactttt ttttttttgta gattatgcat cctggttttg ggtggtgggt   1260
tcctgatgtc aggaatataa atttagcctg ctgatttagg tagcactgcc ggtgcacact   1320 ttggttttttg aatacttgta gtcttccagc ttccttgtaga actggtacaa tgtgggccat   1380
atataagaag ggctgtcaac tagcacatgc tcactaatta gtctaaacat ttatgttttt   1440
attcattcag gtcaggtgca atcatagaag tagttaatga caatacttta gttgttctaa   1500
tattatttat gtatggactc aaattaacat gcaaaacata tgagattagt ggcatgcatt   1560 cttttttctta atagtggaaa atacgagata atgataactg tgaagctctg ttagtactct   1620
tcattactct atttgagtgg cagcatatct catgctagcc ataaagcaag ttctagacgt   1680
attctgttgt taattacttg tagctatata acccaaccta gtcattccag cttatgtctc   1740
ttagagatca tgtttattag cacctcaaga ttttcctctgc acagtatagt aactatcgaa   1800
aaagatatta tttctttgtt ttaattgac aaccttcacg tgctacttat ttttgcagag   1860
taaatctata ggcc                                                    1874

<210> SEQ ID NO 2
<211> LENGTH: 1487
<212> TYPE: DNA
<213> ORGANISM: Oryza sativa

<400> SEQUENCE: 2
ctgcagccat caaagccgcc ccaccaacac aactccccac gaggccccga gcatatcatc     60
gccttcgccg caaagtccca acactagcgg cgaccggcga ggactccggc ggcgacgtgg    120
gtgggactga gaagcgccgc cgctgacacc agcgagacga ggcggcgacc tccgttgacg    180
gtaacctacc taccaacctc gccattcctc tccaaactgt tgtgctgctg tctagatctc    240
ccacactaca ctagttactc ctcgtagatc tcggctacct ggctcaagat ccggggtcag    300
atccgggtcc ggggatttc tttgtgccct atggctgtat tttggcgtct gtggctgatg    360
acagcgtgtg ttctcgagtg cggatgcaat ctgagttata taggcaaatg gccttgtcaa    420
ctcgggcagc ggcattgctt tgctcagtgt gtttgaatgt gctgaaattc atgtagtagg    480
ctgtaggctg tgcattcctt gatttgcgtc ttgcataatt cactggtgga ttttctaaac    540
```

-continued

| | |
|---|---|
| ctaacaagtt taaaattaga ccattcaacc aaagacagga ggaataagtg aagctgttgt | 600 |
| agtcacagct tatggccgat ccaaaatttg ttaggaatgt gaatatgtga tgctacaaac | 660 |
| atatccttgt aagctaccat gctatttatc atgttccatc atggtgattg gtgagcactc | 720 |
| atgaaaattt cagatccaaa cctagtgtta catgtggatt tgtgctctgc aatctatcgc | 780 |
| cagtaataaa atggttgagt gatccagcta ctacaaaatc acattgcata cttttttttt | 840 |
| tgtagattat gcatcctggt tttgggtggt gggttcctga tgtcaggaat ataaatttag | 900 |
| cctgctgatt taggtagcac tgccggtgca cactttggtt tttgaatact tgtagtcttc | 960 |
| cagcttcttg tagaactggt acaatgtggg ccaaatataa gaagggctgt caactagcac | 1020 |
| atgctcacta attagtctaa acatttatgt ttttattcat tcaggtcagg tgcaatcata | 1080 |
| gaagtagtta atgacaatac tttagttgtt ctaatattat ttatgtatgg actcaaatta | 1140 |
| acatgcaaaa catatgagat tagtggcatg cattcttttt cttaatagtg gaaaatacga | 1200 |
| gataatgata actgtgaagc tctgttagta ctcttcatta ctctatttga gtggcagcat | 1260 |
| atctcatgct agccataaag caagttctag acgtattctg ttgttaatta cttgtagcta | 1320 |
| tataacccaa cctagtcatt ccagcttatg tctcttagag atcatgttta ttagcacctc | 1380 |
| aagatttcct ctgcacagta tagtaactat cgaaaagat attatttctt tgttttaat | 1440 |
| tgacaacctt cacgtgctac ttattttgc agagtaaatc tatggcc | 1487 |

<210> SEQ ID NO 3
<211> LENGTH: 2515
<212> TYPE: DNA
<213> ORGANISM: Oryza sativa

<400> SEQUENCE: 3

| | |
|---|---|
| gccgcagcca taggtttgcc agatgaccaa tctcttttta cgtaacactt agcacgtatt | 60 |
| attagaaaaa aaacacccaa aattttagaa tttcactatg gaatgttttt ctctgtcgcc | 120 |
| atgatctagc aagcaaaact acaatacatt gagttctctg attgatgaac tgattatgat | 180 |
| tccaacccaa ttaagcttta cttgcttttc tttccagggg ttgcccacat gtggtcatga | 240 |
| tcaacacagc tggggggggag gaacaaaatt aataaagcga gttgatcaaa cagcgcaaga | 300 |
| acagcaagca gcttttcagg cacacatggg ggtgtactaa aatagcctga aattcttcca | 360 |
| tccttcccca aaatcaagat cccatcggat catatcatca gtcaggcaga cgacagcgca | 420 |
| ggcaacagct gttcctggct gtgttgctgc catgcctagc ttaggttaat tgtgctgatc | 480 |
| ccacttgatt agcgcactaa tcgcaccttt aatccgtatt gcccgtgtgt gttaatgtat | 540 |
| gtgcaccgtt aacgcgataa ttagttaaga gcccggacac catggttttc ttttctatg | 600 |
| aagaaatgtt caaatggaag gataatatat ccttttgaaa aagcattgat taccaagatt | 660 |
| tgtttggaaa caaatttatc agcattatga agaaaatcaa ttcatgcacg aaattgaaga | 720 |
| aaattaatgt gatccaaacg aggcctaaca tggttttttct tttcttaaat ataaaaggt | 780 |
| gtaaattaca catatatcgt tacctcaaat catactggat tatatttaaa aaaatctctc | 840 |
| agattatttt taaaaaagca tatggatgga tgcatgtaga ctatatgtac aagtacaata | 900 |
| ttactactaa ctcatgtaaa aagaaccgat catatatatt acaaaacact ggcatacgac | 960 |
| ctagctgtca actaggctaa caatataatt atggaagagg agtgagaaaa aacaagtaaa | 1020 |
| ataaggcaca aaggaagaat atagagacac attttttaatt ttaaattgtg ttcttgtaaa | 1080 |
| gaataaattt tgtttgcat tataaaacta agttatatta gtacatttta agtggtttac | 1140 |
| ttgtatagca aataagttac atgctctacc atgtcgagat attataggtg atgaaccggt | 1200 |

```
tataatcacc ttgaggtatg cactagcacc cttgacgagc actctactac ctgcctacgc   1260
tcgtgaaaat ggtcattgac caaatatgtg gataaagatg acgtcttctt catcatgctt   1320
gtatgaaaat tttcataggt gctcctattt caatccatgc tggactgtga aagaaatac    1380 taccatctag tttgtttttc agctcgacat aaccgaagtt gatgagagat cgtgttagga   1440
gaactcgtag gctcctcctt tttttttct  tttttttgcc aaatgccgta caacgtatta   1500
gagaaaaaat aatttatagg taaattttt  atgtatgtat tcttagcgat ttaaaattga   1560
atgtaaaaga taaacttaga tgaaaaagaa cctgaaagca aaccttaaac tttaaatttt   1620
ggaagcggga ttcagtatag acaaacccat agagccatag agggtcctat ttttgttttg   1680
ggacagacag gcgccaactt ctcagttctc agattcagag cgtaaccgta cccaagaagt   1740 gaaaaagaa  aaatcagagc gcgcttaatt gtgtccaaaa aatgattgtg tggccctagt   1800
cgaggaaccc ccctctcttc tcttatctac ccctccccct ccccccctcg actccgcgtc   1860
gactccactc tcgcctcctc gcgactcgga gttcaccgcc gccaccgcct ccgccgccga   1920 tctcccgtc  ccgccgcgcc gccgccaccg tcctccctcc tccggccgca tcccggtga    1980 gcatccatct gcgtgtcctc ttcctcatct ctccctcccc acgcacgcac gcacgtactc   2040
gtagcttctg ttcactgttc tagatctgga tacttttcgc ttcattcgcc ttattaaacc   2100
ttgatgctgg tagcagtttg tttgtttgtg ttttttttcc cgcgcgcaaa aaatgtttgt   2160 gggggggtgga actgaatcac atgctccacg tctaggtccg ccacctgagt ttgccttgca  2220
tcacggttta gtgcttgatt cttttgtgcgc ggttgattat cgcgtactct ttttgctcta  2280
caagttctag atctcggtgt gtcggactat cgatatgtag ttttgcatac tctgttttgt   2340
tttctgttcg ctgcaagttt tgatgtgcca aatattagca gttgatcttt tgagattttg   2400
atttcctgga gggtttgcgt ctagtttctg ttggaaaatg gccatttcgt gacgtgttgc    2460
ggcgcatgcc tgttgttctg ttttttgcgtc aggaattcag aaccagtagg aggcc         2515

<210> SEQ ID NO 4
<211> LENGTH: 1246
<212> TYPE: DNA
<213> ORGANISM: Oryza sativa

<400> SEQUENCE: 4
tgctggtctg cgcatgcgaa gcgcgaagag gaggaacaat ggtggctcat ggagaaagag    60
gggtggtggc ggtgcgtgga gtggaagcta gtgattgccg gtggcctaag gagtttgttg   120
tcgacacaat tctctaccga gttcatcaca tttttttctc taagtactat tgacatgtgt   180
gggtcactag tcattataaa gaactagcta aaggtctgtg cgttgtaaca aatattataa    240
gagataaaag taaaagcaaa attacaagg  ttataacata gttaattatt taggtataca    300
atgccatata caaacaaaa  gtattcacat gtgaggatct tatggctcca catgtcagct    360
tgtgacatta aggtaaaact cgaacatcaa cattagcatc attttaagta gtaagtatag    420
atatacttca tccggattaa taatacttgt catttttggat aaggacatgg ttttcaaaaa   480
acaacattta ccactatttt ttatataata tatgtagtaa tattaataaa tataaaaatt    540
tattgaagta cttttaagaa caatctatat gtacggtcac cgtatttcca agacaaatat    600
ttcagatgta atttatagtt aatgtttga  agtttaacg  ataggcttat ccaaaacggt    660
aagtactact acaccggagg aagtgcatgt gtagttttat agagcatggt aaaaaaaaat    720
ggagataaag gcaggtgtag tggagtatct atcttcccac cttggcgtaa aagaaaagaa    780
```

| | |
|---|---|
| aatctgcagt ctgtgtcgtc tcctccggtc cttgcgcgca agaccgagtc gcggctgccg | 840 |
| atctccatct gccgatcgag cagagcatag caggggatcc tggtaagcat ccacatcctc | 900 |
| tttccttctc agaattcatc tatctctttc tggggatctg gaatttgctt gcgttcatta | 960 |
| accctagctt ctcttctaga ctagatctgg aagaagctct tggatctctt agttccagag | 1020 |
| ccttaacctt agtacaagta gcacttcgtt tgttccccaa aagttggatc cgcccctgcg | 1080 |
| agttttgtgg tttttccggg tgcaaactag tatagtagag cttaagaaat gaagtactca | 1140 |
| tcaatgattt agttgaagaa atgcgtcgtc gtcgagttgt atagcaacaa tgatcaggca | 1200 |
| ctactacttg ttaaagtatt aactctctgc agctcttctg taggcc | 1246 |

<210> SEQ ID NO 5
<211> LENGTH: 2724
<212> TYPE: DNA
<213> ORGANISM: Oryza sativa

<400> SEQUENCE: 5

| | |
|---|---|
| tataattggc atccaaacta agcccaaata gacaaaagcg cggcagctgg acaccttgct | 60 |
| attcatcctg gactttcgca acgggaaact catgggccct caaggtgatt ggcagcgcag | 120 |
| gccgccttcg ccgtgctagc aggattttttt ttattagttt aaattttttat ttacaaaaaa | 180 |
| aaaattattc aaactatat tctatccgtc ctataaaaaa cgaatctaat accggatgtg | 240 |
| atatattcta gtacgatgaa tctggataga tatatgtcta gattcgtagt actataatgt | 300 |
| gttacatccg gtattagttt ggttttttaa tgaaacgaag ggagtacgta tttagtagtg | 360 |
| catctctacc ctctcttaaa cggtttttat gacataacac acgactgtgg atgcaagtta | 420 |
| gcagccacgc ggagggaggt caaccatttt acaggcagcc ctcttccgct ctcctaaata | 480 |
| caaatggttg ctcgtaaaat cttcgtgcgg ccattaacat acaccaacgg atatgtcaca | 540 |
| tatgccacgt cataaaaaaa atcatcttgg aggtgtagat ttataaagag | 600 |
| taaatttaac aaaattaaag ataagttgat caaattacag taaaactaca tatttaagat | 660 |
| aatgtaccac aaaactatat atttaacatt aaattttttcc caaaactaga tattcaaggt | 720 |
| ggagtgccgt aaaactatag atatagaaaa atgttatcac aaaattacgg gtgtttacaa | 780 |
| ctcaaacata gaagaattta aaacctaaat tttgtaattt tgtaattttg tgattttta | 840 |
| cgatacttgg tcataaacct aaaattatgc gataaactta ggctgcgttc aggataaggg | 900 |
| gttgggaacc cgaagcacgc attatcgcat aattaattaa gtgttaactt ttttaaaaaa | 960 |
| atgattatga ttttttaaaa ctacctttt atagaatttt ttctgcaaaa acctcacggt | 1020 |
| ttattaattt gaaaacgtg caggcggaaa acgagagata tgagttggaa aaaattagag | 1080 |
| gaataacaca acattagtgt caaatatata cttataaata tgtagttttg ctataattta | 1140 |
| gttataaagc atatgcagtt ttgtaaaatt taatcattta taaagctttg aaaaaatatt | 1200 |
| tttgtttaac atttttattaa taactaaaat taaaatatatt ctgcaagcaa ccggatcgct | 1260 |
| gtcagcctgt caccgcctca ccggcgaagg ctgacggggt cacgggagta ggttgcgcgg | 1320 |
| tcggcttcca ccgcacgcca gcacgccccg tccaaaccag ccggtggccc accggccatt | 1380 |
| aagaaaccga ctccgacgtg gccgttccgg tttcggcacc gaaagtccgt ccgtttccgt | 1440 |
| tgccaacttg ccaataccca ccgacccggc acgccagtcc aggtcaggtc agacaccttc | 1500 |
| ggcttggctg gctcacctcg tgctctgccg tgccgtgacg gtgccatgtc acgttcaaac | 1560 |
| ggcgaggcaa aggggaggag ggtagctgag cacacacgcg gtccgtgctt ctgcaggcga | 1620 |
| aggtgacgcc gcagaagact ggtccaacgg ggcggcttcc acgcataaaa cggctcccct | 1680 |

```
tgctgcgctt tccgtttcgg ctctcccatt tgtctcgcgc tcgctgtctc gcgtcagcgg      1740
cggagctctc tagaaggagc agaggagtcc cccccaagcg atcgattcga tccccctccgc     1800 cgccgatcgc ctcgccgaag tctccgaggt ataagcccgt tcgatctctc cctctccctc     1860
tccatccttg tttcgatctg atccgtggaa tcgcttcgct ggatcgccgg tagagcttcc     1920
cgtgctttgt tgtccgggtg attttccgg ggaatttcgc gctgttttcg tggactgttt      1980
gtgttgacct cggcgtttgg acgcttgcgg ttgatagctg tatcctctca tgactagcaa     2040
gggaattcat ggcgtttgtg tactgtatgt tgtatagtct gatccttggt cgggttgtat     2100
gctgcagttg cagacagcag agcagttcca atatcacttc tggagatgat ctcaaactgc     2160
ataataccta ttctaatact ttctatttcc tttctaacaa tccgctgcgc agctagttgt     2220
atgttacttc agtcgatact tgcatcatgc atccagaatt ccagacaaat agttgtatgt    2280
tacttcatgt tgtgtttttt cctttgttaa catgaaacct ctgatgtgtc acatcgtgat    2340
tgtgtttacc tttattgcgt agttttttt aaaagatcca tactgcctta ctgaaatcaa     2400
agcgaactca aatgaaaatt ctttcttatt ttgcatgatc atacattcag tcccaggtgc    2460
cacttctaat ggttagtccc atgttgtgtt ttttcctata cctgatcagt tccctaatga    2520
tatgatctgt attttattgg ttgttcgttg gcatgttgta aatgtttagt gattgctact    2580
tcattttttt tatcatgcac tttatttggg cccaggagta agctcggtgg cacttaagca    2640
aaacagtgct taagttaata tgcacaataa ttgattttg aatgcattct gaatactgat     2700
atttgttgca gaaacacttg agcc                                           2724

<210> SEQ ID NO 6
<211> LENGTH: 1774
<212> TYPE: DNA
<213> ORGANISM: Zea mays

<400> SEQUENCE: 6
taaaggttaa attgtcatcc ctaatcgtga tgactttacc caaaaccgtt tgtacagaag       60
caaaaaaacg gcggtcattt tggatggttt tcgcctgaac ttttttggctt tgccctccga    120 gcctcttttt tctgctatga caactgtcgc cgcgcacata aatgaaacgg acgccgttcc     180
tcttctcccc tcttccatag catagcagag caggcgcacg gcgcaccgca cacctcactg     240 ccgctcccctt ctcgtctcct ctcctctcct ctcctcggcg gatccggcac cgacccaccg    300
cccctctgct cgctccttcc gccggaatcg ctgctcctct ctgtgctgtc gatttgtgcg    360
gcgactgtta gtttggttcg gtcccatcct tctgttggta agtgatacta ccatgccctg    420
agaggaagag gtgcttttgc cttttgctttt ttagttttag attagagttg tttcattca    480 gttgatcctg ccctgagagt gagatttac ctttcactct tagttttaga ttatagttcg     540
tttcatttca gttgatcttg atcatacctt gccctgagaa tgagatttat gtcctaatat    600
gcagcagtaa tcttgctagc ttgatcggat cctgtactaa ccagttcgtg tcagctagta    660
ttttccgctc ctttgatcaa gagggggag gaggcagtgc tccatgtgtc atacccggat     720
aatcggaagc agaaatggat ttgatatgcg gtggaggcgc ttgttactag tcctgggtgg    780
ctagatctca tctcatggtt ctggtttcaa gtggaaagtc cgttactcgt gggaaacgaa    840
tgactcgcat agttttttcgt tggatgtttt tgctcatcgc gtggatagcc gtgggcccac    900
aatagtttct gtaaatcttg aggccaggtt ggtctagatc ccatccagtg attattgtga    960
ccttgtgctt ggcagcctaa ctaggtgctt actgagcttt tattgggcga accttacata   1020
```

| | |
|---|---|
| gcttttccta gctaataaaa atatgtatat tcatgtcaaa tactgctaac ccgagccaga | 1080 |
| atctttgtca ggttatcttg gtctaaacag ctcaatcttt caaccagcca gctattgttt | 1140 |
| ttccccccct tcccttttgg cataaacaat ccagtttata atctcttgct agctggaatc | 1200 |
| ggaatgatgg gcgccactac tgacttcttg ctggcacatg gactttaggc tcccatcgtc | 1260 |
| tacagctaaa tgaagtatcc agcataggct ggatgtgcag cagcagcaat aattctgatc | 1320 |
| cagtacagct tcttcatttt gttaggctca gtagcacatg ggcgggcaag tgagcatgtc | 1380 |
| tctgcctgac aggacacctt atgccagctt atagctagta tacagagcat aattaatcca | 1440 |
| ctttataatt gattcagtgt tatatgcttt tccttcaaag tcgttagtcc tatttaccag | 1500 |
| ctggtccttg ttcagagatt cattgatggt aataatcttg ctgcaacctg agttcctgac | 1560 |
| ctagagacaa ggcctgctaa atacaacctt gcattccttt tacttggcta tcacaaactg | 1620 |
| ctcttagtta tcattatgtg cctgaaaacc atatggcctt tctcttatta acttaaattt | 1680 |
| ccaagccatc tagcatgaac taggttaaaa aaattgtgct ttaacaagtg aatatttgag | 1740 |
| atggtctctg aattcagatt gtctgtgcag atcc | 1774 |

<210> SEQ ID NO 7
<211> LENGTH: 1544
<212> TYPE: DNA
<213> ORGANISM: Zea mays

<400> SEQUENCE: 7

| | |
|---|---|
| gcctggtctg ctagcgacgg ctgtggccca caagcccatg gaccacggct gccgcccgtg | 60 |
| ccccacccgc cctgtcatcc gacgaggacg cgtgccggat tcggcaccga aagcttcggt | 120 |
| ccggcagccg ccctccgcca aatccgcccg ctggagccct ccgacagatt tttatcatcg | 180 |
| ggcgcccacg cgtctccatt gacccgggca ggggcgaggt caagagggcg aaccgttggc | 240 |
| cgggtcgccc ccgctatcat gccgtgctgt gacacggcgg caggcggctt cccaacgacg | 300 |
| ctgcgtgcgc acccgcgggc cgcagccgcc ccaggcgcct gcataccagt ccaaccaggc | 360 |
| ggcctcgtat aaagaggttc cccacttggg ctgccgctct cccatttgtc tcgcgcttcg | 420 |
| ctctcacgct cgcgtcaccg gagctctcca gaaccgaacc ccaactgccc aagggcgagc | 480 |
| gatccgaacc cctcggcggc ttcgtcaacg acgccgaggt atagccgtgt cccccccccc | 540 |
| ccccccctct gatctgccat cgattcgatc cgaggaagcg atccgttgta gacagtcggt | 600 |
| tcgatagatc cccgctcgac cttcccgtcg gtgttgactt cgatttttg gtgtcgattt | 660 |
| tgctgttttt gtcatgctcg tttcggctct gggattcgga taggtggtct ggtatggtgt | 720 |
| aaattgatcc agcgtaacga gcaaaagcta ccggcgtatg tgtagcgtag tcctgtactc | 780 |
| ctactatgtg tcctatgatt tctacagtac ctctgttgtg ttttgtttga ttggattctc | 840 |
| tggtttatgt gatggaagtt aaccatgtcc agttactcag tcagttcatg ggagtatata | 900 |
| tgattcagag tgtgttgagt tgcatgctat gctggtccgt agcagagtag cggaaccgga | 960 |
| aaattgctct cagatcactc ggtgaagaac tggagatgac ttcaagcagt gaaatcacgc | 1020 |
| tgtttctgtt gataattcag acgaaatgtg gctcaaacat ctaattaacc attttcctca | 1080 |
| acgaaactgc ccccctgat cctcctaccc aaataggagt gtggtttcag acgattcatg | 1140 |
| taatgggtat atatatgtga tatgtttgtt ggcataaaa aaaatgaaac gtgcatggtc | 1200 |
| tgatctctga tggtagcaga caaatttacg gcctatcaag tatcaagata atgaataatt | 1260 |
| tgtattatca gatagcaccg aagtctgtct ctgcgaattg cttaaaagtt tatacttgca | 1320 |
| tgagtcgagt atcagttttc tttaacacgg agtcaagttc agttgcttaa tcatgaacac | 1380 |

```
                                          -continued
ttgtgcacct tagttttggc tgatgactgg catgttgcaa tttggtgtca tcatactttt    1440
ttgtggggtt tatctgactc catggacatt tgaaggatta acactgctgc agatacattc    1500
aaatacattc tgaatatagc attgctgcag aacactttga ggac                     1544
```

ACTIN REGULATORY ELEMENTS FOR USE IN PLANTS

This application is a Divisional of U.S. patent application Ser. No. 10/950,233, filed 24 Sep. 2004 and published as U.S. Patent Application No. 7,408,054, which claims priority to U.S. Provisional Patent Application No. 60/505,949, filed 25 Sep. 2003, both of which are incorporated by reference in their entirety herein.

INCORPORATION OF SEQUENCE LISTING

Two copies of the sequence listing (Seq. Listing Copy 1 and Seq. Listing Copy 2) and a computer-readable form of the sequence listing, all on CD-ROMs, each containing the file named pa_01298.rpt, which is 16,783 bytes (measured in MS Windows®) and was created on May 5, 2007, are hereby incorporated by reference.

FIELD OF THE INVENTION

The invention relates to the field of plant molecular biology and plant genetic engineering and polynucleotide molecules useful for the expression of transgenes in plants.

BACKGROUND

One of the goals of plant genetic engineering is to produce plants with agronomically desirable characteristics or traits. The proper expression of a desirable transgene in a transgenic plant is one way to achieve this goal. Regulatory elements such as promoters, leaders, and introns are non-coding polynucleotide molecules which play an integral part in the overall expression of genes in living cells. Isolated regulatory elements that function in plants are therefore useful for modifying plant phenotypes through the methods of genetic engineering.

Many regulatory elements are available and are useful for providing good overall expression of a transgene. For example, constitutive promoters such as P-FMV, the promoter from the 35S transcript of the Figwort mosaic virus (U.S. Pat. No. 6,051,753); P-CaMV 35S, the promoter from the 35S RNA transcript of the Cauliflower mosaic virus (U.S. Pat. No. 5,530,196); P-Rice Actin 1, the promoter from the actin 1 gene of *Oryza sativa* (U.S. Pat. 5,641,876); and P-NOS, the promoter from the nopaline synthase gene of *Agrobacterium tumefaciens* are known to provide some level of gene expression in most or all of the tissues of a plant during most or all of the plant's lifespan. While previous work has provided a number of regulatory elements useful to affect gene expression in transgenic plants, there is still a great need for novel regulatory elements with beneficial expression characteristics. Many previously identified regulatory elements fail to provide the patterns or levels of expression required to fully realize the benefits of expression of selected genes in transgenic crop plants.

Spatial organization within the eukaryotic cell and directed movements of the cell contents are mediated by the cytoskeleton, a network of filamentous protein polymers that permeates the cytosol. Actin is one of the three major families of proteins making up the cytoskeleton. Members of this multi-gene family have been reported in almost all eukaryotic species including yeast, humans, mouse, *Drosophila*, tobacco, maize, rice, soybean, potato and *Arabidopsis*. Plant actins are encoded by a multi-gene family, constituted by a number of different isotypes.

We hypothesized that the regulatory elements from an actin gene might have a constitutive expression pattern and that the regulatory elements could be useful to direct expression of a transgene such as a glyphosate resistant 5-enolpyruvylshikimate-3-phosphate synthase (EPSPS) transgene to produce a glyphosate tolerant plant. The efficient production of glyphosate tolerant plants requires the use of regulatory elements capable of directing transgene expression in all tissues including the most sensitive reproductive organs such as anthers and meristem tissues. The present invention thus provides such regulatory elements isolated from actin genes of *Oryza sativa* and *Zea mays*.

SUMMARY

In one embodiment the invention provides polynucleotide molecules isolated from *Oryza sativa* and *Zea mays* useful for modulating transgene expression in plants. In another embodiment the invention provides expression constructs containing the polynucleotide molecules useful for modulating transgene expression in plants. In another embodiment the invention provides transgenic plants and seeds containing the polynucleotide molecules useful for modulating transgene expression in plants.

DETAILED DESCRIPTION

Figure 1:
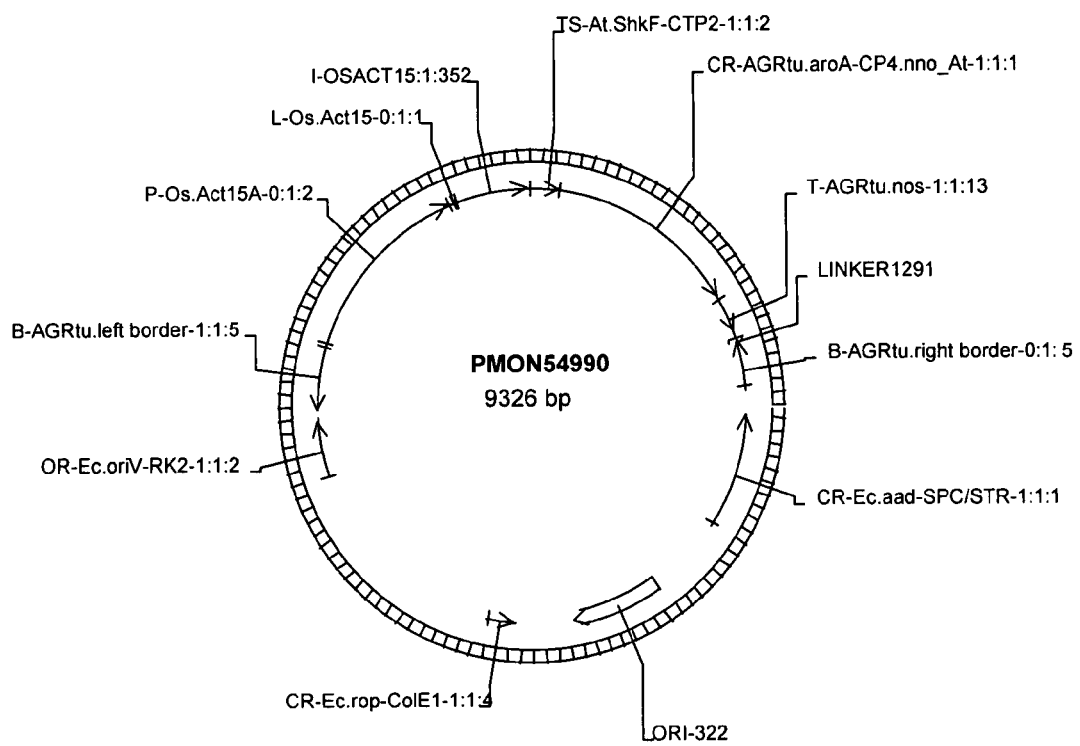
FIG. 1: Construct pMON54990 containing the P-Os-Act15a cassette.

The following definitions and methods are provided to better define the present invention and to guide those of ordinary skill in the art in the practice of the present invention. Unless otherwise noted, terms are to be understood according to conventional usage by those of ordinary skill in the relevant art.

The invention disclosed herein provides polynucleotide molecules having gene regulatory activity from *Oryza sativa* and *Zea mays*. The design, construction, and use of these polynucleotide molecules are one object of this invention. The polynucleotide sequences of these polynucleotide molecules are provided as SEQ ID NO: 1-7. These polynucleotide molecules are capable of affecting the transcription of operably linked transcribable polynucleotide molecules in both vegetative and reproductive tissues of plants and therefore can selectively regulate expression of transgenes in these tissues.

As used herein, the term "polynucleotide molecule" refers to the single- or double-stranded DNA or RNA of genomic or synthetic origin, i.e., a polymer of deoxyribonucleotide or ribonucleotide bases, respectively, read from the 5' (upstream) end to the 3' (downstream) end.

As used herein, the term "polynucleotide sequence" refers to the sequence of a polynucleotide molecule. The nomenclature for DNA bases as set forth at 37 CFR §1.822 is used.

As used herein, the term "gene regulatory activity" refers to a polynucleotide molecule capable of affecting transcription or translation of an operably linked transcribable polynucleotide molecule. An isolated polynucleotide molecule having gene regulatory activity may provide temporal or spatial expression or modulate levels and rates of expression of the operably linked transcribable polynucleotide molecule. An isolated polynucleotide molecule having gene regulatory activity may comprise a promoter, intron, leader, or 3' transcriptional termination region.

As used herein, the term "regulatory element" refers to an isolated polynucleotide molecule capable of having gene regulatory activity. A regulatory element may comprise a promoter, intron, leader, or 3' transcriptional termination region.

As used herein, the term "promoter" refers to a polynucleotide molecule that is involved in recognition and binding of RNA polymerase II and other proteins (trans-acting transcription factors) to initiate transcription. A "plant promoter" is a native or non-native promoter that is functional in plant cells. A plant promoter can be used as a 5' regulatory element for modulating expression of an operably linked gene or genes. Plant promoters may be defined by their temporal, spatial, or developmental expression pattern.

A promoter comprises subfragments that have promoter activity. Subfragments may comprise enhancer domains and may be useful for constructing chimeric promoters. Subfragments of SEQ ID NO: 1 comprise at least about 75, 85, 90, 95, 110, 125, 250, 400, 750, 1000, 1300, 1500, and 1700 contiguous nucleotides of the polynucleotide sequence of SEQ ID NO: 1-7. Subfragments of SEQ ID NO: 2 comprise at least about 95, 110, 125, 250, 400, 750, 1000, and 1300 contiguous nucleotides of the polynucleotide sequence of SEQ ID NO: 2. Subfragments of SEQ ID NO: 3 comprise at least about 95, 110, 125, 250, 400, 750, 1000, 1300, 1500, and 1800 contiguous nucleotides of the polynucleotide sequence of SEQ ID NO: 3. Subfragments of SEQ ID NO: 4 comprise at least about 95, 110, 125, 250, 400, 750, and 1000 contiguous nucleotides of the polynucleotide sequence of SEQ ID NO: 4. Subfragments of SEQ ID NO: 5 comprise at least about 95, 110, 125, 250, 400, 750, 1000, 1300, 1500, 1800, and 2500 contiguous nucleotides of the polynucleotide sequence of SEQ ID NO: 5. Subfragments of SEQ ID NO: 6 comprise at least about 95, 110, 125, 250, 400, 750, 1000, 1300, and 1500 contiguous nucleotides of the polynucleotide sequence of SEQ ID NO: 6. Subfragments of SEQ ID NO: 7 comprise at least about 95, 110, 125, 250, 400, 750, 1000, and 1300 contiguous nucleotides of the polynucleotide sequence of SEQ ID NO: 7.

As used herein, the term "enhancer domain" refers to a cis-acting transcriptional regulatory element, a.k.a. cis-element, which confers an aspect of the overall control of gene expression. An enhancer domain may function to bind transcription factors, trans-acting protein factors that regulate transcription. Some enhancer domains bind more than one transcription factor, and transcription factors may interact with different affinities with more than one enhancer domain. Enhancer domains can be identified by a number of techniques, including deletion analysis, i.e., deleting one or more nucleotides from the 5' end or internal to a promoter; DNA binding protein analysis using DNase I footprinting, methylation interference, electrophoresis mobility-shift assays, in vivo genomic footprinting by ligation-mediated PCR, and other conventional assays; or by DNA sequence similarity analysis with known cis-element motifs by conventional DNA sequence comparison methods. The fine structure of an enhancer domain can be further studied by mutagenesis (or substitution) of one or more nucleotides or by other conventional methods. Enhancer domains can be obtained by chemical synthesis or by isolation from promoters that include such elements, and they can be synthesized with additional flanking nucleotides that contain useful restriction enzyme sites to facilitate subsequence manipulation. Thus, the design, construction, and use of enhancer domains according to the methods disclosed herein for modulating the expression of operably linked polynucleotide molecules are encompassed by the present invention.

As used herein, the term "chimeric" refers to the product of the fusion of portions of two or more different polynucleotide molecules. As used herein, the term "chimeric promoter" refers to a promoter produced through the manipulation of known promoters or other polynucleotide molecules. Such chimeric promoters may combine enhancer domains that can confer or modulate gene expression from one or more promoters, for example, by fusing a heterologous enhancer domain from a first promoter to a second promoter with its own partial or complete regulatory elements. Thus, the design, construction, and use of chimeric promoters according to the methods disclosed herein for modulating the expression of operably linked polynucleotide molecules are encompassed by the present invention.

As used herein, the term "percent sequence identity" refers to the percentage of identical nucleotides in a linear polynucleotide sequence of a reference polynucleotide molecule (or its complementary strand) as compared to a test polynucleotide molecule (or its complementary strand) when the two sequences are optimally aligned (with appropriate nucleotide insertions, deletions, or gaps totaling less than 20 percent of the reference sequence over the window of comparison). Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and preferably by computerized implementations of these algorithms such as GAP, BESTFIT, FASTA, and TFASTA available as part of the GCG® Wisconsin Package® (Accelrys Inc., Burlington, Mass.). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence.

As used herein, the term "substantial percent sequence identity" refers to a percent sequence identity of at least about 70% sequence identity, at least about 80% sequence identity, at least about 90% sequence identity, or even greater sequence identity, such as about 98% or about 99% sequence identity. Thus, one embodiment of the invention is a polynucleotide molecule that has at least about 70% sequence identity, at least about 80% sequence identity, at least about 90% sequence identity, or even greater sequence identity, such as about 98% or about 99% sequence identity with a polynucleotide sequence described herein. Polynucleotide molecules that are capable of regulating transcription of operably linked transcribable polynucleotide molecules and have a substantial percent sequence identity to the polynucleotide sequences of the polynucleotide molecules provided herein are encompassed within the scope of this invention.

Promoter Isolation and Modification Methods

Any number of methods well known to those skilled in the art can be used to isolate fragments of a promoter disclosed herein. For example, PCR (polymerase chain reaction) technology can be used to amplify flanking regions from a genomic library of a plant using publicly available sequence information. A number of methods are known to those of skill in the art to amplify unknown polynucleotide molecules adjacent to a core region of known polynucleotide sequence. Methods include but are not limited to inverse PCR (IPCR), vectorette PCR, Y-shaped PCR, and genome walking approaches. Polynucleotide fragments can also be obtained by other techniques such as by directly synthesizing the fragment by chemical means, as is commonly practiced by using an automated oligonucleotide synthesizer. For the present invention, the polynucleotide molecules were isolated from genomic DNA by designing PCR primers based on available sequence information.

Novel chimeric promoters can be designed or engineered by a number of methods. For example, a chimeric promoter may be produced by fusing an enhancer domain from a first promoter to a second promoter. The resultant chimeric promoter may have novel expression properties relative to the first or second promoters. Novel chimeric promoters can be constructed such that the enhancer domain from a first promoter is fused at the 5' end, at the 3' end, or at any position internal to the second promoter. The location of the enhancer domain fusion relative to the second promoter may cause the resultant chimeric promoter to have novel expression properties relative to a fusion made at a different location.

Those of skill in the art are familiar with the standard resource materials that describe specific conditions and procedures for the construction, manipulation, and isolation of macromolecules (e.g., polynucleotide molecules, plasmids, etc.), as well as the generation of recombinant organisms and the screening and isolation of polynucleotide molecules.

Constructs

As used herein, the term "construct" refers to any recombinant polynucleotide molecule such as a plasmid, cosmid, virus, autonomously replicating polynucleotide molecule, phage, or linear or circular single-stranded or double-stranded DNA or RNA polynucleotide molecule, derived from any source, capable of genomic integration or autonomous replication, comprising a polynucleotide molecule where one or more polynucleotide molecule has been operably linked.

As used herein, the term "operably linked" refers to a first polynucleotide molecule, such as a promoter, connected with a second transcribable polynucleotide molecule, such as a gene of interest, where the polynucleotide molecules are so arranged that the first polynucleotide molecule affects the function of the second polynucleotide molecule. The two polynucleotide molecules may be part of a single contiguous polynucleotide molecule and may be adjacent. For example, a promoter is operably linked to a gene of interest if the promoter regulates or mediates transcription of the gene of interest in a cell.

As used herein, the term "transcribable polynucleotide molecule" refers to any polynucleotide molecule capable of being transcribed into a RNA molecule. Methods are known for introducing constructs into a cell in such a manner that the transcribable polynucleotide molecule is transcribed into a functional mRNA molecule that is translated and therefore expressed as a protein product. Constructs may also be constructed to be capable of expressing antisense RNA molecules, in order to inhibit translation of a specific RNA molecule of interest. For the practice of the present invention, conventional compositions and methods for preparing and using constructs and host cells are well known to one skilled in the art, see for example, *Molecular Cloning: A Laboratory Manual, 3rd edition Volumes* 1, 2, *and* 3 (2000) J. F. Sambrook, D. W. Russell, and N. Irwin, Cold Spring Harbor Laboratory Press.

Constructs of the present invention would typically contain a promoter operably linked to a transcribable polynucleotide molecule operably linked to a 3' transcription termination polynucleotide molecule. In addition, constructs may include but are not limited to additional regulatory polynucleotide molecules from the 3'-untranslated region (3' UTR) of plant genes (e.g., a 3' UTR to increase mRNA stability of the mRNA, such as the PI-II termination region of potato or the octopine or nopaline synthase 3' termination regions). Constructs may include but are not limited to the 5' untranslated regions (5' UTR) of an mRNA polynucleotide molecule which can play an important role in translation initiation and can also be a genetic component in a plant expression construct. For example, non-translated 5' leader polynucleotide molecules derived from heat shock protein genes have been demonstrated to enhance gene expression in plants (see for example, U.S. Pat. Nos. 5,659,122 and 5,362,865, all of which are hereby incorporated by reference). These additional upstream and downstream regulatory polynucleotide molecules may be derived from a source that is native or heterologous with respect to the other elements present on the promoter construct.

Thus, one embodiment of the invention is a promoter such as provided in SEQ ID NO: 1-7, operably linked to a transcribable polynucleotide molecule so as to direct transcription of said transcribable polynucleotide molecule at a desired level or in a desired tissue or developmental pattern upon introduction of said construct into a plant cell. In some cases, the transcribable polynucleotide molecule comprises a protein-coding region of a gene, and the promoter provides for transcription of a functional mRNA molecule that is translated and expressed as a protein product. Constructs may also be constructed for transcription of antisense RNA molecules or other similar inhibitory RNA in order to inhibit expression of a specific RNA molecule of interest in a target host cell.

Exemplary transcribable polynucleotide molecules for incorporation into constructs of the present invention include, for example, polynucleotide molecules or genes from a species other than the target gene species, or even genes that originate with or are present in the same species, but are incorporated into recipient cells by genetic engineering methods rather than classical reproduction or breeding techniques. Exogenous gene or genetic element is intended to refer to any gene or polynucleotide molecule that is introduced into a recipient cell. The type of polynucleotide molecule included in the exogenous polynucleotide molecule can include a polynucleotide molecule that is already present in the plant cell, a polynucleotide molecule from another plant, a polynucleotide molecule from a different organism, or a polynucleotide molecule generated externally, such as a polynucleotide molecule containing an antisense message of a gene, or a polynucleotide molecule encoding an artificial or modified version of a gene.

The promoters of the present invention can be incorporated into a construct using marker genes as described and tested in transient analyses that provide an indication of gene expression in stable plant systems. As used herein the term "marker gene" refers to any transcribable polynucleotide molecule whose expression can be screened for or scored in some way. Methods of testing for marker gene expression in transient assays are known to those of skill in the art. Transient expression of marker genes has been reported using a variety of plants, tissues, and DNA delivery systems. For example, types of transient analyses can include but are not limited to direct gene delivery via electroporation or particle bombardment of tissues in any transient plant assay using any plant species of interest. Such transient systems would include but are not limited to electroporation of protoplasts from a variety of tissue sources or particle bombardment of specific tissues of interest. The present invention encompasses the use of any transient expression system to evaluate promoters or promoter fragments operably linked to any transcribable polynucleotide molecules, including but not limited to selected reporter genes, marker genes, or genes of agronomic interest. Examples of plant tissues envisioned to test in transients via an appropriate delivery system would include but are not limited to leaf base tissues, callus, cotyledons, roots, endosperm, embryos, floral tissue, pollen, and epidermal tissue.

Any scorable or screenable marker gene can be used in a transient assay. Exemplary marker genes for transient analyses of the promoters or promoter fragments of the present invention include a GUS gene (U.S. Pat. No. 5,599,670, hereby incorporated by reference) or a GFP gene (U.S. Pat. Nos. 5,491,084 and 6,146,826, both of which are hereby incorporated by reference). The constructs containing the promoters or promoter fragments operably linked to a marker gene are delivered to the tissues and the tissues are analyzed by the appropriate mechanism, depending on the marker. The quantitative or qualitative analyses are used as a tool to evaluate the potential expression profile of the promoters or promoter fragments when operatively linked to genes of agronomic interest in stable plants.

Thus, in one preferred embodiment, a polynucleotide molecule of the present invention as shown in SEQ ID NO: 1-7 is incorporated into a DNA construct such that a polynucleotide molecule of the present invention is operably linked to a transcribable polynucleotide molecule that provides for a selectable, screenable, or scorable marker. Markers for use in the practice of the present invention include, but are not limited to transcribable polynucleotide molecules encoding β-glucuronidase (GUS), green fluorescent protein (GFP), luciferase (LUC), proteins that confer antibiotic resistance, or proteins that confer herbicide tolerance. Useful antibiotic resistance markers, including those encoding proteins conferring resistance to kanamycin (nptII), hygromycin B (aph IV), streptomycin or spectinomycin (aad, spec/strep) and gentamycin (aac3 and aacC4) are known in the art. Herbicides for which transgenic plant tolerance has been demonstrated and the method of the present invention can be applied, include but are not limited to: glyphosate, glufosinate, sulfonylureas, imidazolinones, bromoxynil, delapon, cyclohezanedione, protoporphyrionogen oxidase inhibitors, and isoxasflutole herbicides. Polynucleotide molecules encoding proteins involved in herbicide tolerance are known in the art, and include, but are not limited to a polynucleotide molecule encoding 5-enolpyruvylshikimate-3-phosphate synthase (EPSPS) described in U.S. Pat. Nos. 5,627,061, 5,633,435, 6,040,497 and in 5,094,945 for glyphosate tolerance, all of which are hereby incorporated by reference; polynucleotides encoding a glyphosate oxidoreductase and a glyphosate-N-acetyl transferase (GOX, U.S. Pat. No. 5,463,175 and GAT, U.S. Patent publication 20030083480, herein incorporated by reference); a polynucleotide molecule encoding bromoxynil nitrilase (Bxn) described in U.S. Pat. No. 4,810,648 for Bromoxynil tolerance, which is hereby incorporated by reference; a polynucleotide molecule encoding phytoene desaturase (crtI) described in Misawa et al, (1993) *Plant J.* 4:833-840 and Misawa et al, (1994) *Plant J.* 6:481-489 for norflurazon tolerance; a polynucleotide molecule encoding acetohydroxyacid synthase (AHAS, aka ALS) described in Sathasiivan et al. (1990) *Nucl. Acids Res.* 18:2188-2193 for tolerance to sulfonylurea herbicides; and the bar gene described in DeBlock, et al. (1987) *EMBO J.* 6:2513-2519 for glufosinate and bialaphos tolerance; resistant hydroxyphenyl pyruvate dehydrogenase (HPPD, U.S. Pat. No. 6,768,044). The promoter of the present invention can express genes that encode for phosphinothricin acetyltransferase, glyphosate resistant EPSPS, aminoglycoside phosphotransferase, hydroxyphenyl pyruvate dehydrogenase, hygromycin phosphotransferase, neomycin phosphotransferase, dalapon dehalogenase, bromoxynil resistant nitrilase, anthranilate synthase, glyphosate oxidoreductase and glyphosate-N-acetyl transferase.

Where plastid targeting is necessary, for example, the EPSPS enzyme functions in a plant chloroplast, therefore, DNA molecules encoding a chloroplast transit peptide (CTP) are engineered into a DNA molecule encoding an EPSPS protein to encode a fusion protein of the CTP to the N terminus of an EPSPS creating a chimeric molecule. A chimeric polynucleic acid coding sequence is comprised of two or more open reading frames joined in-frame that encode a chimeric protein, for example, a chloroplast transit peptide and an EPSPS enzyme. A chimeric gene refers to the multiple genetic elements derived from heterologous sources operably linked to comprise a gene. In the present invention the DNA construct expresses a chimeric CTP-EPSPS protein that directs the glyphosate resistant EPSPS protein into the plant chloroplast. In a native plant EPSPS gene, chloroplast transit peptide regions are contained in the native coding sequence (for example, CTP2, Klee et al., Mol. Gen. Genet. 210:47-442, 1987). The CTP is cleaved from the EPSPS enzyme at the chloroplast membrane to create a "mature EPSPS or EPSPS enzyme" that refers to the polypeptide sequence of the processed protein product remaining after the chloroplast transit peptide has been removed. The production of glyphosate tolerant plants by expression of a fusion protein comprising an amino-terminal CTP with a glyphosate resistant EPSPS enzyme is well known by those skilled in the art, (U.S. Pat. Nos. 5,627,061, 5,633,435, 5,312,910, EP 0218571, EP 189707, EP 508909, and EP 924299). Those skilled in the art will recognize that various chimeric constructs can be made that utilize the functionality of a particular CTP to import glyphosate resistant EPSPS enzymes into the plant cell chloroplast.

In one embodiment of the invention, a polynucleotide molecule as shown in SEQ ID NO: 1-7 is incorporated into a construct such that a polynucleotide molecule of the present invention is operably linked to a transcribable polynucleotide molecule that is a gene of agronomic interest. As used herein, the term "gene of agronomic interest" refers to a transcribable polynucleotide. molecule that includes but is not limited to a gene that provides a desirable characteristic associated with plant morphology, physiology, growth and development, yield, nutritional enhancement, disease or pest resistance, or environmental or chemical tolerance. The expression of a gene of agronomic interest is desirable in order to confer an agronomically important trait. A gene of agronomic interest that provides a beneficial agronomic trait to crop plants may be, for example, including, but not limited to genetic elements comprising herbicide resistance (U.S. Pat. Nos. 5,633,435 and 5,463,175), increased yield (U.S. Pat. No. 5,716,837), insect control (U.S. Pat. Nos. 6,063,597; 6,063,756; 6,093,695; 5,942,664; and 6,110,464), fungal disease resistance (U.S. Pat. Nos. 5,516,671; 5,773,696; 6,121,436; 6,316,407, and 6,506,962), virus resistance (U.S. Pat. Nos. 5,304,730 and 6,013,864), nematode resistance (U.S. Pat. No. 6,228,992), bacterial disease resistance (U.S. Pat. No. 5,516,671), starch production (U.S. Pat. Nos. 5,750,876 and 6,476,295), modified oils production (U.S. Pat. No. 6,444,876), high oil production (U.S. Pat. Nos. 5,608,149 and 6,476,295), modified fatty acid content (U.S. Pat. No. 6,537,750), high protein production (U.S. Pat. No. 6,380,466), fruit ripening (U.S. Pat. No. 5,512,466), enhanced animal and human nutrition (U.S. Pat. Nos. 5,985,605 and 6,171,640), biopolymers (U.S. Pat. Nos. 5,958,745 and U.S. Patent Publication No. US20030028917), environmental stress resistance (U.S. Pat. No. 6,072,103), pharmaceutical peptides (U.S. Pat. No. 6,080,560), improved processing traits (U.S. Pat. No. 6,476,295), improved digestibility (U.S. Pat. No. 6,531,648) low raffinose (U.S. Pat. No. 6,166,292), industrial enzyme production (U.S. Pat. No. 5,543,576), improved flavor (U.S. Pat. No. 6,011,199), nitrogen fixation (U.S. Pat. No. 5,229,114), hybrid seed production (U.S. Pat. No. 5,689,041), and biofuel production (U.S. Pat. No. 5,998,700). The genetic elements, methods, and transgenes described in the patents listed above are hereby incorporated by reference.

Alternatively, a transcribable polynucleotide molecule can effect the above mentioned phenotypes by encoding a RNA molecule that causes the targeted inhibition of expression of an endogenous gene, for example via antisense, inhibitory RNA (RNAi), or cosuppression-mediated mechanisms. The RNA could also be a catalytic RNA molecule (i.e., a ribozyme) engineered to cleave a desired endogenous mRNA product. Thus, any polynucleotide molecule that encodes a protein or mRNA that expresses a phenotype or morphology change of interest may be useful for the practice of the present invention.

The constructs of the present invention are generally double Ti plasmid border DNA constructs that have the right border (RB or AGRtu.RB) and left border (LB or AGRtu.LB) regions of the Ti plasmid isolated from *Agrobacterium tumefaciens* comprising a T-DNA, that along with transfer molecules provided by the *Agrobacterium* cells, permits the integration of the T-DNA into the genome of a plant cell. The constructs also contain the plasmid backbone DNA segments that provide replication function and antibiotic selection in bacterial cells, for example, an *Escherichia coli* origin of replication such as ori322, a broad host range origin of replication such as oriV or oriRi, and a coding region for a selectable marker such as Spec/Strp that encodes for Tn7 aminoglycoside adenyltransferase (aadA) conferring resistance to spectinomycin or streptomycin, or a gentamicin (Gm, Gent) selectable marker gene. For plant transformation, the host bacterial strain is often *Agrobacterium tumefaciens* ABI, C58, or LBA4404, however, other strains known to those skilled in the art of plant transformation can function in the present invention.

Transformed Plants and Plant Cells

As used herein, the term "transformed" refers to a cell, tissue, organ, or organism into which has been introduced a foreign polynucleotide molecule, such as a construct. The introduced polynucleotide molecule may be integrated into the genomic DNA of the recipient cell, tissue, organ, or organism such that the introduced polynucleotide molecule is inherited by subsequent progeny. A "transgenic" or "transformed" cell or organism also includes progeny of the cell or organism and progeny produced from a breeding program employing such a transgenic plant as a parent in a cross and exhibiting an altered phenotype resulting from the presence of a foreign polynucleotide molecule. A plant transformation construct containing a promoter of the present invention may be introduced into plants by any plant transformation method. Methods and materials for transforming plants by introducing a plant expression construct into a plant genome in the practice of this invention can include any of the well-known and demonstrated methods including electroporation as illustrated in U.S. Pat. No. 5,384,253; microprojectile bombardment as illustrated in U.S. Pat. Nos. 5,015,580; 5,550,318; 5,538,880; 6,160,208; 6,399,861; and 6,403,865; *Agrobacterium*-mediated transformation as illustrated in U.S. Pat. Nos. 5,824,877; 5,591,616; 5,981,840; and 6,384,301; and protoplast transformation as illustrated in U.S. Pat. No. 5,508,184, all of which are hereby incorporated by reference.

Methods for specifically transforming dicots are well known to those skilled in the art. Transformation and plant regeneration using these methods have been described for a number of crops including, but not limited to, cotton (*Gossypium hirsutum*), soybean (*Glycine max*), peanut (*Arachis hypogaea*), and members of the genus *Brassica*.

Methods for transforming monocots are well known to those skilled in the art. Transformation and plant regeneration using these methods have been described for a number of crops including, but not limited to, barley (*Hordeum vulgarae*); maize (*Zea mays*); oats (*Avena sativa*); orchard grass (*Dactylis glomerata*); rice (*Oryza sativa*, including indica and japonica varieties); sorghum (*Sorghum bicolor*); sugar cane (*Saccharum* sp); tall fescue (*Festuca arundinacea*); turfgrass species (e.g. species: *Agrostis stolonifera, Poa pratensis, Stenotaphrum secundatum*); wheat (*Triticum aestivum*), and alfalfa (*Medicago sativa*). It is apparent to those of skill in the art that a number of transformation methodologies can be used and modified for production of stable transgenic plants from any number of target crops of interest.

The transformed plants are analyzed for the presence of the genes of interest and the expression level and/or profile conferred by the promoters of the present invention. Those of skill in the art are aware of the numerous methods available for the analysis of transformed plants. For example, methods for plant analysis include, but are not limited to Southern blots or northern blots, PCR-based approaches, biochemical analyses, phenotypic screening methods, field evaluations, and immunodiagnostic assays.

The seeds of this invention can be harvested from fertile transgenic plants and be used to grow progeny generations of transformed plants of this invention including hybrid plant lines comprising the construct of this invention and expressing a gene of agronomic interest.

The present invention also provides for parts of the plants of the present invention. Plant parts, without limitation, include seed, endosperm, ovule and pollen. In a particularly preferred embodiment of the present invention, the plant part is a seed.

Still yet another aspect of the invention is a method of inhibiting weed growth in a field of transgenic crop plants comprising first planting the transgenic plants transformed with an expression cassette comprising an isolated polynucleotide molecule having gene regulatory activity and comprising a polynucleotide sequence selected from the group consisting of SEQ ID NO: 1-7 and operably linked to a DNA molecule encoding a glyphosate tolerance gene and then applying glyphosate to the field at an application rate that inhibits the growth of weeds, wherein the growth and yield of the transgenic crop plant is not substantially affected by the glyphosate application. The glyphosate application rate is the effective rate necessary to control weeds in a particular glyphosate tolerant crop; these rates may range from 8 ounces/acre to 256 ounces/acre, preferably 16 ounces/acre to 128 ounces/acre, and more preferably 32 ounces/acre to 96 ounces/acre. The glyphosate is applied at least once during the growth of the glyphosate tolerant crop and may be applied 2, 3, or 4 times during the growth of the crop or more as necessary to control weeds in the field.

The following examples are included to demonstrate preferred embodiments of the invention. It should be appreciated by those of skill in the art that the techniques disclosed in the examples that follow represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

Example 1

Constitutive Gene Identification

Four actin promoters were isolated from rice and two actin promoters were cloned from maize. Genomic DNA was generated from corn (*Zea mays*) and rice (*Oryza sativa*) tissue using standard methods familiar to one skilled in the art. The genomic libraries were prepared according to manufacturer instructions (GenomeWalker™, CLONTECH Laboratories, Inc, Palo Alto, Calif.). In separate reactions, genomic DNA was subjected to restriction enzyme digestion overnight at 37° C. with the following blunt-end endonucleases: EcoRV, ScaI, DraI, PvuII, or StuI (CLONTECH Laboratories, Inc. Palo Alto, Calif.). The reaction mixtures were extracted with phenol:chloroform, ethanol precipitated, and resuspended in 10 mM Tris buffer pH 8.5. The purified blunt-ended genomic DNA fragments were then ligated to the GenomeWalker™ adaptors. Ligation of the resulting DNA fragments to adaptors was done according to manufacturer protocol. The GenomeWalker™ sublibraries were aliquoted and stored at −20° C.

Four rice actin genes were aligned to design a gene-specific primer capable of annealing to multiple actin gene sequences. Three corn actin genes were aligned to design a gene-specific primer capable of annealing to multiple actin genes. Genomic DNA from corn and rice ligated to the GenomeWalker™adaptor was subjected to PCR amplification in separate reactions with either the rice or corn gene-specific primer and a primer designed to anneal to the GenomeWalker™ adaptor. Standard protocols provided by the manufacturer were used. Those of skill in the art are aware of the variations in PCR conditions including choice of polymerase, cycling conditions, and concentrations of the reaction components. PCR products were cloned into pUC19 and the DNA insert was sequenced for each clone. The presence of an actin gene sequence in the insert sequence was used to identify the upstream promoter region.

Example 2

Constructs

The isolated promoters were cloned into an appropriate plant expression vector for the subsequent characterization of the promoter in plants. The DNA fragments resulting from the nested PCR amplification described above were isolated and gel purified using methods familiar to those skilled in the art. The purified DNA was digested with one or more restriction endonuclease(s) to permit ligation into a suitable cloning or expression vector. The promoter fragments were incorporated into a plant expression vector by positioning the promoter fragments in linkage with a reporter gene by restriction enzyme digestion and ligation using methods well known in the art. The purified DNA of the present invention was ligated as a NotI/NcoI fragment into a vector containing the necessary plant expression elements, including the GUS or At-CP4-EPSPS transgene operably linked to the promoter. An aliquot of the ligation reaction was transformed into a suitable *E. coli* host such as DH10B and the cells were plated on selection medium (100 µg/ml spectinomycin). Bacterial transformants were selected, grown in liquid culture, and the plasmid DNA was isolated using a commercially available kit such as the Qiaprep Spin Miniprep Kit (Qiagen Corp., Valencia, Calif.). Purified plasmid containing the predicted insert size was DNA sequenced in both directions using the dye terminator method and oligonucleotide primers designed to anneal to the region of the vector bordering the promoter insertion site. Additional oligonucleotide primers for further DNA sequencing of the promoter were then prepared based on the sequence produced from the results of the first DNA sequencing reaction. This was repeated until a full-length sequence of the isolated promoter was produced.

Example 3

Promoter Characterization in Transient Systems

Corn protoplasts transformed with a vector containing a promoter operably liked to the GUS transgene were analyzed for GUS expression levels, measured by GUS activity as MU (pMol/ng of Total Protein). GUS expression levels of the actin promoters in protoplasts were compared to GUS expression levels in protoplasts transformed with a vector having the Os-actin 1 (ract1) promoter driving GUS and a vector having the Os-actin 2 promoter driving GUS. Protoplasts transformed with a vector containing only the luciferase transgene (LUC) were used as a negative control for GUS activity. Data are provided in Table 1.

TABLE 1

| GUS activity measurements in corn protoplasts | | |
|---|---|---|
| Promoter operably linked to GUS | Seq ID Num | GUS activity |
| P-e35S | | 0.380 |
| P-Os-actin 1 | | 0.383 |
| P-Os-actin 2 | | 0.341 |
| P-Os-Act15a | SEQ ID NO: 1 | 0.479 |
| P-Os-Act15b | SEQ ID NO: 2 | 0.336 |
| P-Os-Act16 | SEQ ID NO: 3 | 0.343 |
| P-Os-Act18 | SEQ ID NO: 4 | 0.322 |
| P-Os-Act31 | SEQ ID NO: 5 | 0.958 |
| P-Zm-Act31 | SEQ ID NO: 6 | 1.156 |
| P-Zm-Act33 | SEQ ID NO: 7 | 0.710 |
| LUC | | 0.218 |

Corn protoplasts transformed with a vector containing a promoter operably linked to the At-CP4-EPSPS transgene were analyzed for CP4 expression levels, measured as CP4-EPSPS accumulation (ng of CP4/mg of total protein). CP4-EPSPS expression levels of the actin promoters in protoplasts were compared to CP4-EPSPS expression levels in protoplasts transformed with a vector having the Os-actin 1 (ract1) promoter driving At-CP4-EPSPS and a vector having the e35S promoter driving At-CP4-EPSPS. Protoplasts transformed with a vector containing only the luciferase transgene (LUC) were used as a negative control for GUS activity. Data are provided in Table 2.

TABLE 2

CP4-EPSPS accumulation measurements in corn protoplasts

Figure 2:
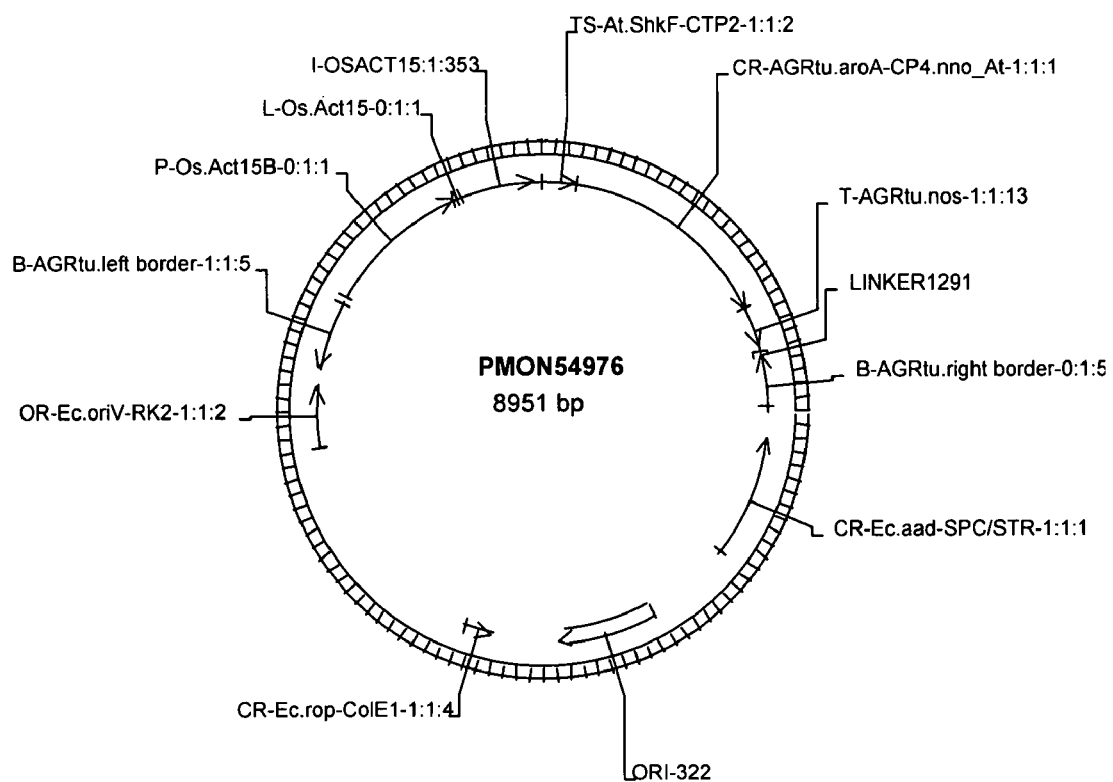
FIG. 2: Construct pMON54976 containing the P-Os-Act15b cassette.
Figure 3:
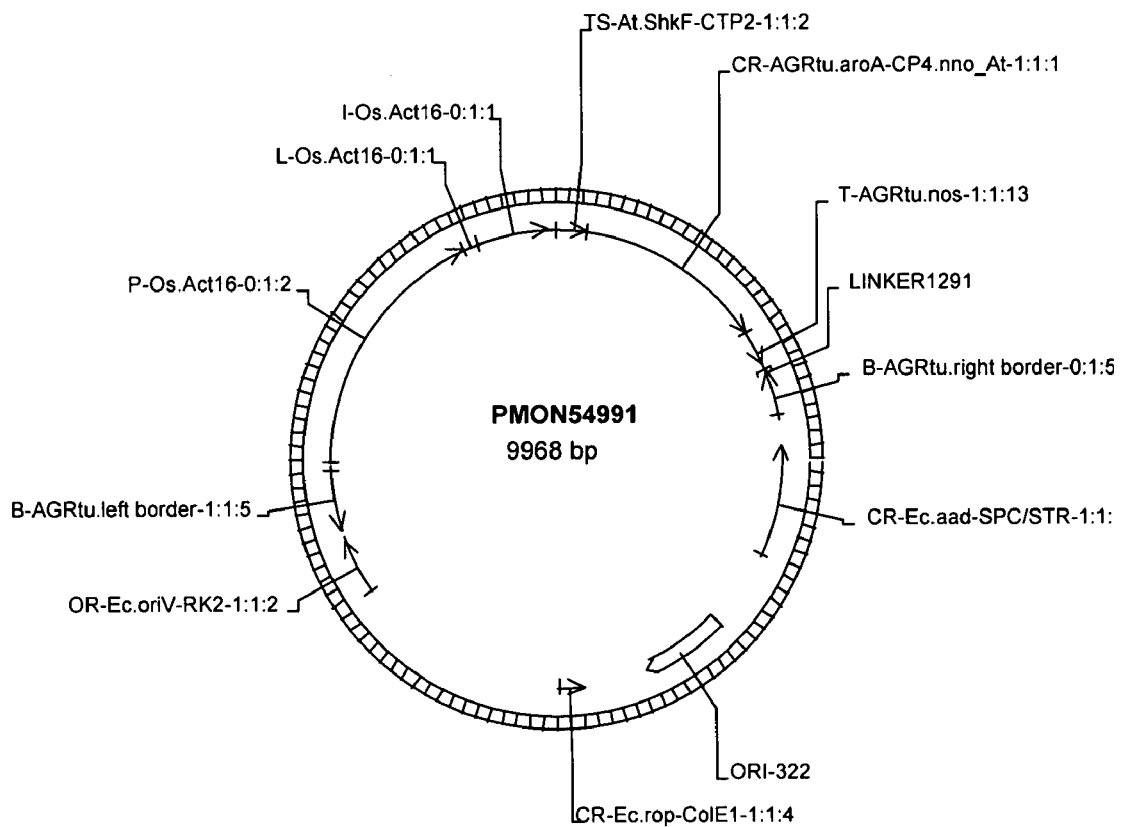
FIG. 3: Construct pMON54991 containing the P-Os-Act16 cassette.
Figure 4:
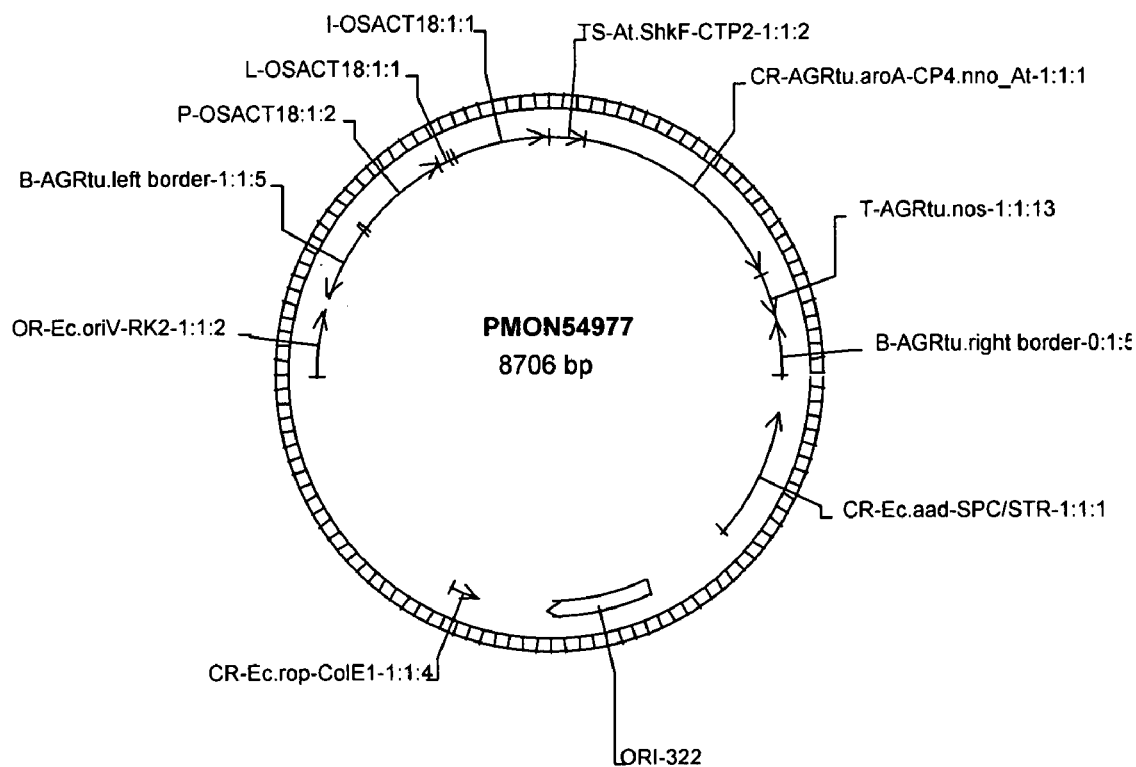
FIG. 4: Construct pMON54977 containing the P-Os-Act18 cassette.
Figure 5:
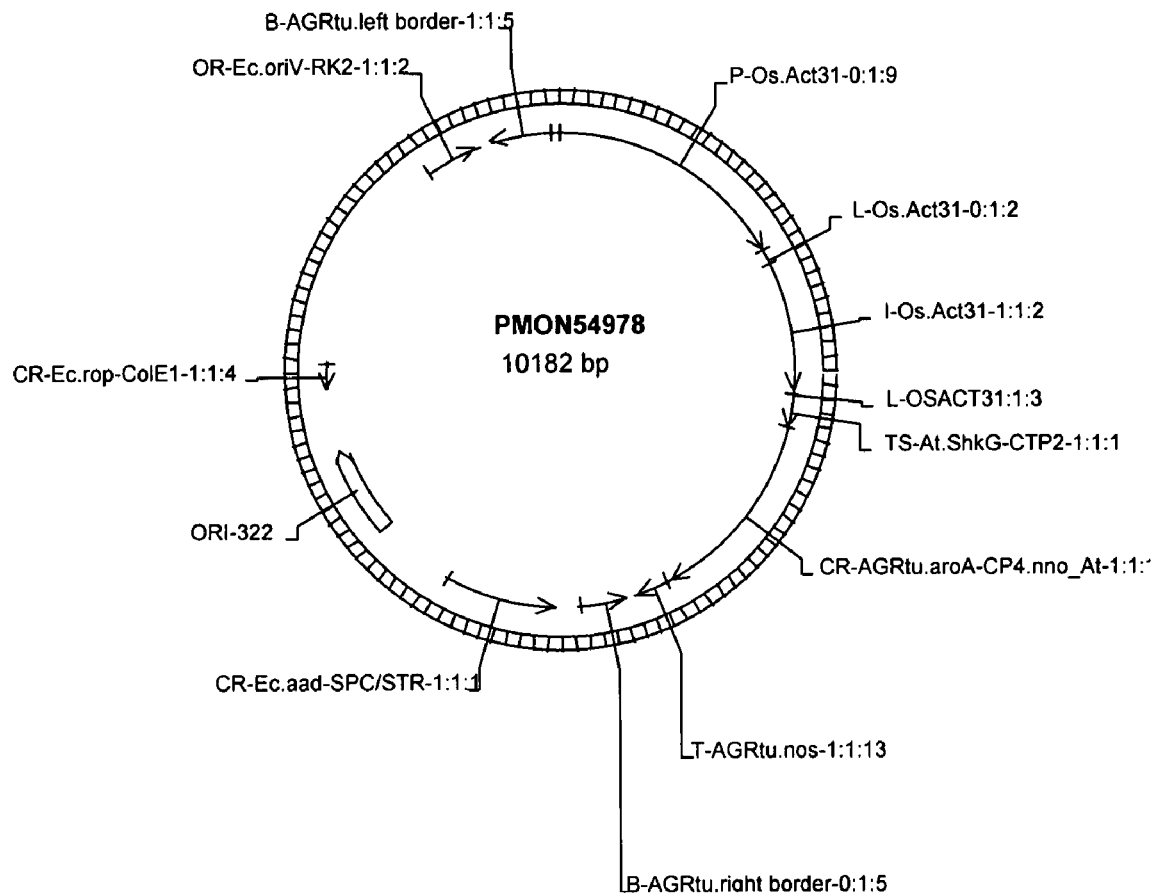
FIG. 5: Construct pMON54978 containing the P-Os-Act31 cassette.
Figure 6:
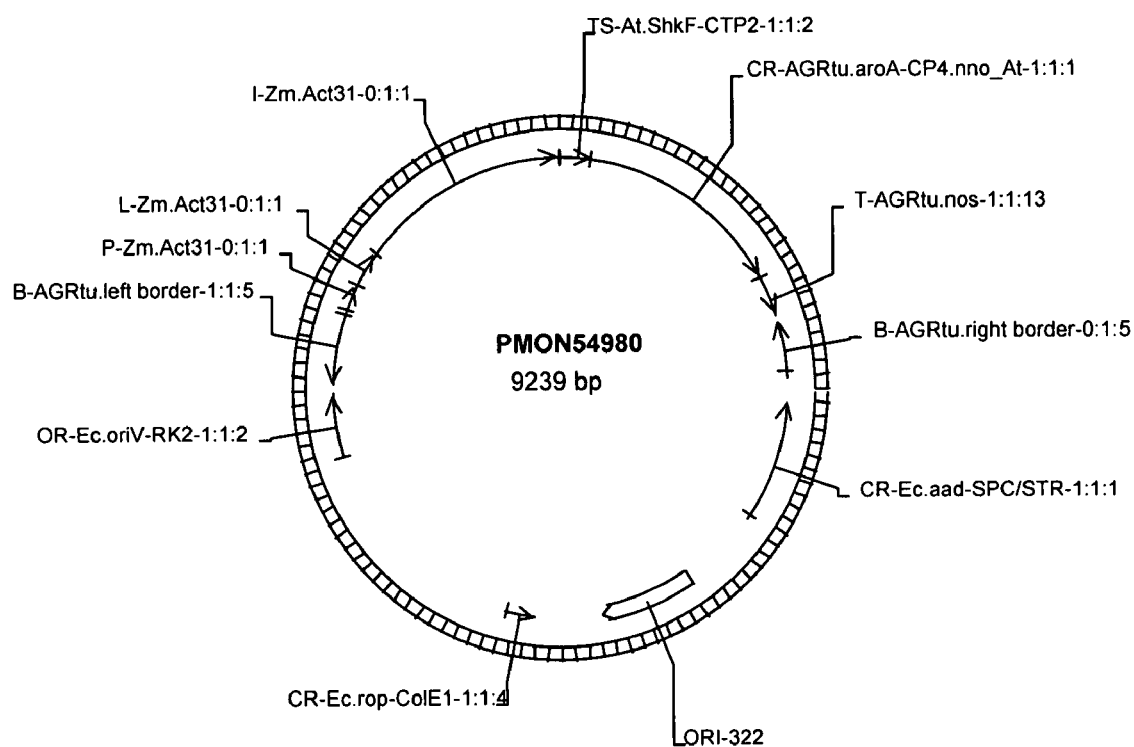
FIG. 6: Construct pMON54980 containing the P-Zm-Act31 cassette.
Figure 7:
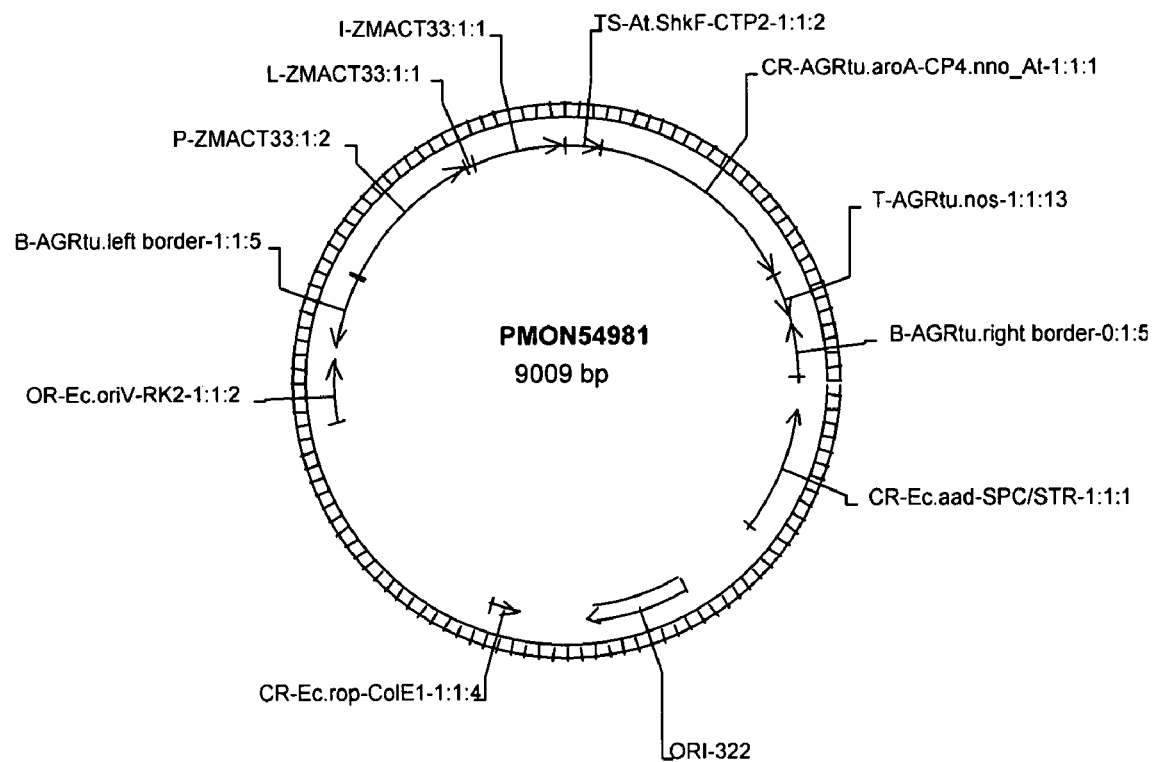
FIG. 7: Construct pMON54981 containing the P-Zm-Act33 cassette.

| Promoter operably linked to At-CP4-EPSPS | Related Figure | CP4-EPSPS accumulation |
|---|---|---|
| P-e35S | None | 7.516 |
| P-Os-actin 1 | None | 2.256 |
| P-Os-actin 2 | None | 2.749 |
| P-Os-Act15a | FIG. 1 | 0.850 |
| P-Os-Act15b | FIG. 2 | 2.505 |
| P-Os-Act16 | FIG. 3 | 1.227 |
| P-Os-Act18 | FIG. 4 | 1.792 |
| P-Os-Act31 | FIG. 5 | 4.588 |
| P-Zm-Act31 | FIG. 6 | 4.714 |
| P-Zm-Act33 | FIG. 7 | 0.504 |
| LUC | None | 0.793 |

Example 4

Promoter Characterization in Transgenic Plants

Transgenic corn plants transformed with a vector containing a promoter operably linked to the CP4-EPSPS transgene were analyzed for transformation efficiency, copy number, and transgene expression level. Transformants were analyzed for transformation efficiency measured as the percent of explants produced (embryos that regenerated to form plants) compared to the total transformed. Genomic DNA from transgenic plants was used to determine the percent of single copy events out of the total number of transgenic plants analyzed. Single copy events were used to determine CP4-EPSPS transgene expression levels, measured as the percent of CP4-EPSPS accumulation relative to Roundup Ready® corn line NK603. CP4-EPSPS expression levels of the actin promoters were compared to CP4-EPSPS expression levels in transgenic plants transformed with a vector having the Os-actin 1 (ract1) promoter driving CP4-EPSPS and a vector having the e35S promoter driving CP4-EPSPS. Data are provided in Table 3.

TABLE 3

Measurements of transgenic corn plants

| Promoter operably linked to CP4-EPSPS | Related Figure | Transformation Efficiency | Single Copy Events | CP4-EPSPS accumulation |
|---|---|---|---|---|
| P-e35S | None | 5.4% | 70% | 75.5% |
| P-Os-Act1 | None | 8.2% | 31% | 78.1% |
| P-Os-Act2 | None | 0% | N/A | N/A |
| P-Os-Act15a | FIG. 1 | 5.3% | 59% | 71.7% |
| P-Os-Act16 | FIG. 3 | 5.4% | 52% | 76.9% |
| P-Os-Act18 | FIG. 4 | 5.2% | 32% | 48.7% |
| P-Os-Act31 | FIG. 5 | 6.6% | 38% | 50.5% |
| P-Zm-Act31 | FIG. 6 | 4.5% | 57% | 66.2% |
| P-Zm-Act33 | FIG. 7 | 0% | N/A | N/A |
| P-Os-Act1/Pe35S | None | N/A | N/A | 100% |

Having illustrated and described the principles of the present invention, it should be apparent to persons skilled in the art that the invention can be modified in arrangement and detail without departing from such principles. We claim all modifications that are within the spirit and scope of the appended claims. All publications and published patent documents cited in this specification are incorporated herein by reference to the same extent as if each individual publication or patent application is specifically and individually indicated to be incorporated by reference.

I claim:

1. An isolated nucleic acid molecule having promoter activity and comprising a polynucleotide sequence selected from the group consisting of:
   a) a polynucleotide sequence comprising SEQ ID NO: 6; and
   b) a polynucleotide sequence comprising a fragment of SEQ ID NO: 6, wherein the fragment comprises at least 95 contiguous nucleotides of SEQ ID NO: 6.

2. A DNA construct comprising an isolated polynucleotide molecule having promoter activity and comprising the polynucleotide molecule of claim 1, wherein said isolated polynucleotide molecule is operably linked to a transcribable polynucleotide molecule.

3. The DNA construct of claim 2, wherein said transcribable polynucleotide molecule is a marker gene.

4. The DNA construct of claim 2, wherein said transcribable polynucleotide molecule is a gene of agronomic interest.

5. The DNA construct of claim 4, wherein said gene of agronomic interest is a herbicide tolerance gene selected from the group consisting of genes that encode for phosphinothricin acetyltransferase, glyphosate resistant 5-enolpyruvylshikimate-3-phosphate synthase, hydroxyphenyl pyruvate dehydrogenase, dalapon dehalogenase, bromoxynil resistant nitrilase, anthranilate synthase, glyphosate oxidoreductase and glyphosate-N-acetyl transferase.

6. A transgenic plant stably transformed with the DNA construct of claim 2.

7. The transgenic plant of claim 6, wherein said plant is a monocotyledonous selected from the group consisting of wheat, maize, rye, rice, oat, barley, turfgrass, sorghum, millet and sugarcane.

8. The transgenic plant of claim 6, wherein said plant is a dicotyledonous plant selected from the group consisting of tobacco, tomato, potato, soybean, cotton, canola, sunflower and alfalfa.

9. A seed of said transgenic plant of claim 7, wherein the seed comprises said DNA construct.

10. A seed of said transgenic plant of claim 8, wherein the seed comprises said DNA construct.

11. A method of inhibiting weed growth in a field of transgenic glyphosate tolerant crop plants comprising: i) planting the transgenic plants transformed with an expression cassette comprising an isolated polynucleotide molecule claim 1 operably linked to a DNA molecule encoding a glyphosate tolerance gene and ii) applying glyphosate to the field at an application rate that inhibits the growth of weeds, wherein the growth and yield of the transgenic crop plant is not substantially affected by the glyphosate application.

12. The method of claim 11, wherein said glyphosate tolerance gene is selected from the group consisting of a gene encoding for a glyphosate resistant 5-enolpyruvylshikimate-3-phosphate synthase, a glyphosate oxidoreductase, and a glyphosate-N-acetyltransferase.

13. The method of claim 11, wherein the transgenic plants are capable of tolerating an application rate up to 256 ounces/acre.

14. The method of claim 11, wherein the transgenic plants are capable of tolerating an application rate ranging from 8 ounces/acre to 128 ounces/acre.

15. The method of claim 11, wherein the transgenic plants are capable of tolerating an application rate ranging from 32 ounces/acre to 96 ounces/acre.

16. The method of claim 11, wherein the application of glyphosate is at least once during the growth of the crop.

\* \* \* \* \*